(12) United States Patent
Kennerknecht et al.

(10) Patent No.: US 6,613,545 B1
(45) Date of Patent: Sep. 2, 2003

(54) NUCLEOTIDE SEQUENCES CODING FOR THE EXPORT OF BRANCHED CHAIN AMINO ACIDS, PROCESS FOR THE ISOLATION THEREOF AND USE THEREOF

(75) Inventors: Nicole Kennerknecht, Krefeld (DE); Hermann Sahm, Julich (DE); Lothar Eggeling, Julich (DE); Walter Pfefferle, Halle (DE)

(73) Assignees: Degussa-Huls Aktiengesellschaft, Frankfurt am Main (DE); Forschungszentrum Julich GmgH, Julich (DE)

( * ) Notice: Subject to any disclaimer, the term of this patent is extended or adjusted under 35 U.S.C. 154(b) by 0 days.

(21) Appl. No.: 09/471,803

(22) Filed: Dec. 23, 1999

(30) Foreign Application Priority Data

Oct. 27, 1999 (DE) .......................... 199 51 708

(51) Int. Cl.$^7$ ................................ C12P 21/06
(52) U.S. Cl. ................... 435/69.1; 435/320.1; 435/243; 435/252.3; 536/23.7
(58) Field of Search ...................... 536/23.7; 435/320.1, 435/69.1, 243, 252.3

(56) References Cited

FOREIGN PATENT DOCUMENTS

| CA | 2241111 | 7/1997 |
|----|---------|--------|
| DE | 195 48 222 | 6/1997 |

OTHER PUBLICATIONS

Database EMBL Online, acc. No. 007942, Belitsky et al., "Branched–chain amino acide trasnport protein AZLC," XP 002159588.

Database EMBL, Online, acc. No. 007923, Belitsky et al., "Branched–chain amino acide transport protein AZLD," XP 002159589.

Tausch et al, "Isoleucine uptake in Corynebacterium glutamicum ATCC 13032 is directed by the brnQ gene product," Archives of Microbiology, Bd. 169, No. 4, Apr. 1998, pp. 303–312.

Eggeling et al, Transport mutants and transport genes of Corynebacterium glutamicum, Annals of the New York Academy of Sciences, Bd. 782, 1996, pp. 191–120.

*Primary Examiner*—Jennifer E. Graser
(74) *Attorney, Agent, or Firm*—Michael A. Sanzo; Fitch, Even, Tabin & Flannery

(57) ABSTRACT

This invention relates to isolated polynucleotides containing at least one of the polynucleotide sequences selected from the group a) polynucleotide which is at least 70% identical to a polynucleotide which codes for a polypeptide containing at least one amino acid sequence of SEQ ID no. 3 or 5, b) polynucleotide which codes for a polypeptide which contains an amino acid sequence which is at least 70% identical to the amino acid sequence of SEQ ID no. 3 or 5, c) polynucleotide which is complementary to the polynucleotides of a), b) or c), and d) polynucleotide containing at least 15 successive bases of the polynucleotide sequences of a), b) or c).

wherein the polypeptides exhibit the biological activity of the enzymes for which the brnE or bernF (sic) gene codes and a process for the fermentative production of branched-chain L-amino acids with amplification of the stated genes.

22 Claims, 1 Drawing Sheet

SEQUENCE LISTING

<160> NUMBER OF SEQ ID NOS: 12

<210> SEQ ID NO 1
<211> LENGTH: 1271
<212> TYPE: DNA
<213> ORGANISM: Corynebacterium glutamicum
<220> FEATURE:
<221> NAME/KEY: gene
<222> LOCATION: (101)..(853)
<223> OTHER INFORMATION: brnF
<221> NAME/KEY: gene
<222> LOCATION: (853)..(1176)
<223> OTHER INFORMATION: brnE
<223> OTHER INFORMATION: ATCC14752

<400> SEQUENCE: 1

```
gcgcgatcaa tggaatctag cttcatatat tgcacaatag cctagttgag gtgcgcaaac      60
tggcaacaaa actacccggc aattgtgtga tgattgtagt gtgcaaaaaa cgcaagagat     120
tcattcaagc ctggaggtgt cgccatccaa ggcagccctg gaaccagatg ataaaggtta     180
tcggcgctac gaaatcgcgc aaggtctaaa aacctccctt gctgcaggtt tgggcatgta     240
cccgattggt attgcgtttg gtctcttggt tattcaatac ggctacgaat ggtgggcagc     300
cccactgttt tccggcctga ttttcgcggg ctccaccgaa atgctggtca tcgccctcgt     360
tgtgggcgca gcgcccctgg gcgccatcgc gctcaccaca ttgctggtga acttccgcca     420
cgtattctat gcgttttcat tcccgctgca tgtggtcaaa accccattg cccgtttcta      480
ttcggttttc gcgcttatcg acgaagccta cgcagtcact gcggccaggc ccgcaggctg     540
gtcggcgtgg cgacttatct caatgcaaat agcgtttcac tcctactggg tattcggcgg     600
tctcaccgga gtggcgatcg cagagttgat tccttttgaa attaagggcc tcgagttcgc     660
cctttgctct ctctttgtca cgctgacttt ggattcctgc cgaacgaaaa agcagatccc     720
ttctctgctg ctcgcaggtt tgagcttcac cattgctctt gtggtaattc caggtcaggc     780
cctatttgcg gcgctgctga tcttcttggg tctgttgacc atccggtact tcttcttggg     840
aaaggctgct aaatgacaac tgatttctcc tgtattctcc ttgttgtcgc agtatgtgca     900
gtcattactt ttgcgctccg ggcggttccg ttcttaatcc ttaagcccct acgtgaatca     960
caatttgtgg gcaaaatggc gatgtggatg ccagcaggaa tccttgccat tttgaccgca    1020
tcaacgtttc gcagcaatgc gatagatctg aagactctaa cctttggtct cattgccgtt    1080
gcgattacag tggtggcgca tcttcttggc ggtcgacgca ccttgttgag cgttggcgct    1140
ggcaccatcg ttttgttgg actggtgaat cttttctaaa actgcataaa taacaaaaat    1200
ccgcatgccc tcaatttgaa ggggatgcgg atttttaag gaacctagaa aaggcttaag    1260
cagacagcgc t                                                          1271
```

<210> SEQ ID NO 2
<211> LENGTH: 753
<212> TYPE: DNA
<213> ORGANISM: Corynebacterium glutamicum
<220> FEATURE:
<221> NAME/KEY: CDS
<222> LOCATION: (1)..(753)
<223> OTHER INFORMATION: brnF
<223> OTHER INFORMATION: ATCC14752

<400> SEQUENCE: 2

```
gtg caa aaa acg caa gag att cat tca agc ctg gag gtg tcg cca tcc        48
Met Gln Lys Thr Gln Glu Ile His Ser Ser Leu Glu Val Ser Pro Ser
 1               5                  10                  15 aag gca gcc ctg gaa cca gat gat aaa ggt tat cgg cgc tac gaa atc        96
Lys Ala Ala Leu Glu Pro Asp Asp Lys Gly Tyr Arg Arg Tyr Glu Ile
             20                  25                  30 gcg caa ggt cta aaa acc tcc ctt gct gca ggt ttg ggc atg tac ccg       144
Ala Gln Gly Leu Lys Thr Ser Leu Ala Ala Gly Leu Gly Met Tyr Pro
         35                  40                  45 att ggt att gcg ttt ggt ctc ttg gtt att caa tac ggc tac gaa tgg       192
Ile Gly Ile Ala Phe Gly Leu Leu Val Ile Gln Tyr Gly Tyr Glu Trp
     50                  55                  60 tgg gca gcc cca ctg ttt tcc ggc ctg att ttc gcg ggc tcc acc gaa       240
Trp Ala Ala Pro Leu Phe Ser Gly Leu Ile Phe Ala Gly Ser Thr Glu
 65                  70                  75                  80 atg ctg gtc atc gcc ctc gtt gtg ggc gca gcg ccc ctg ggc gcc atc       288
Met Leu Val Ile Ala Leu Val Val Gly Ala Ala Pro Leu Gly Ala Ile
                 85                  90                  95 gcg ctc acc aca ttg ctg gtg aac ttc cgc cac gta ttc tat gcg ttt       336
Ala Leu Thr Thr Leu Leu Val Asn Phe Arg His Val Phe Tyr Ala Phe
            100                 105                 110 tca ttc ccg ctg cat gtg gtc aaa aac ccc att gcc cgt ttc tat tcg       384
Ser Phe Pro Leu His Val Val Lys Asn Pro Ile Ala Arg Phe Tyr Ser
        115                 120                 125 gtt ttc gcg ctt atc gac gaa gcc tac gca gtc act gcg gcc agg ccc       432
Val Phe Ala Leu Ile Asp Glu Ala Tyr Ala Val Thr Ala Ala Arg Pro
    130                 135                 140 gca ggc tgg tcg gcg tgg cga ctt atc tca atg caa ata gcg ttt cac       480
Ala Gly Trp Ser Ala Trp Arg Leu Ile Ser Met Gln Ile Ala Phe His
145                 150                 155                 160 tcc tac tgg gta ttc ggc ggt ctc acc gga gtg gcg atc gca gag ttg       528
Ser Tyr Trp Val Phe Gly Gly Leu Thr Gly Val Ala Ile Ala Glu Leu
                165                 170                 175 att cct ttt gaa att aag ggc ctc gag ttc gcc ctt tgc tct ctc ttt       576
Ile Pro Phe Glu Ile Lys Gly Leu Glu Phe Ala Leu Cys Ser Leu Phe
            180                 185                 190 gtc acg ctg act ttg gat tcc tgc cga acg aaa aag cag atc cct tct       624
Val Thr Leu Thr Leu Asp Ser Cys Arg Thr Lys Lys Gln Ile Pro Ser
        195                 200                 205 ctg ctg ctc gca ggt ttg agc ttc acc att gct ctt gtg gta att cca       672
Leu Leu Leu Ala Gly Leu Ser Phe Thr Ile Ala Leu Val Val Ile Pro
    210                 215                 220 ggt cag gcc cta ttt gcg gcg ctg ctg atc ttc ttg ggt ctg ttg acc       720
Gly Gln Ala Leu Phe Ala Ala Leu Leu Ile Phe Leu Gly Leu Leu Thr
225                 230                 235                 240 atc cgg tac ttc ttc ttg gga aag gct gct aaa                           753
Ile Arg Tyr Phe Phe Leu Gly Lys Ala Ala Lys
                245                 250
```

<210> SEQ ID NO 3
<211> LENGTH: 251
<212> TYPE: PRT
<213> ORGANISM: Corynebacterium glutamicum
<220> FEATURE:
<223> OTHER INFORMATION: ATCC14752

<400> SEQUENCE: 3

```
Met Gln Lys Thr Gln Glu Ile His Ser Ser Leu Glu Val Ser Pro Ser
 1               5                  10                  15
```

```
Lys Ala Ala Leu Glu Pro Asp Asp Lys Gly Tyr Arg Arg Tyr Glu Ile
                20                  25                  30

Ala Gln Gly Leu Lys Thr Ser Leu Ala Gly Leu Gly Met Tyr Pro
        35                  40                  45

Ile Gly Ile Ala Phe Gly Leu Val Ile Gln Tyr Gly Tyr Glu Trp
    50                  55                  60

Trp Ala Ala Pro Leu Phe Ser Gly Leu Ile Phe Ala Gly Ser Thr Glu
65                  70                  75                  80

Met Leu Val Ile Ala Leu Val Val Gly Ala Pro Leu Gly Ala Ile
                85                  90                  95

Ala Leu Thr Thr Leu Leu Val Asn Phe Arg His Val Phe Tyr Ala Phe
            100                 105                 110

Ser Phe Pro Leu His Val Val Lys Asn Pro Ile Ala Arg Phe Tyr Ser
        115                 120                 125

Val Phe Ala Leu Ile Asp Glu Ala Tyr Ala Val Thr Ala Ala Arg Pro
    130                 135                 140

Ala Gly Trp Ser Ala Trp Arg Leu Ile Ser Met Gln Ile Ala Phe His
145                 150                 155                 160

Ser Tyr Trp Val Phe Gly Gly Leu Thr Gly Val Ala Ile Ala Glu Leu
                165                 170                 175

Ile Pro Phe Glu Ile Lys Gly Leu Glu Phe Ala Leu Cys Ser Leu Phe
            180                 185                 190

Val Thr Leu Thr Leu Asp Ser Cys Arg Thr Lys Lys Gln Ile Pro Ser
        195                 200                 205

Leu Leu Leu Ala Gly Leu Ser Phe Thr Ile Ala Leu Val Val Ile Pro
    210                 215                 220

Gly Gln Ala Leu Phe Ala Ala Leu Leu Ile Phe Leu Gly Leu Leu Thr
225                 230                 235                 240

Ile Arg Tyr Phe Phe Leu Gly Lys Ala Ala Lys
                245                 250

<210> SEQ ID NO 4
<211> LENGTH: 324
<212> TYPE: DNA
<213> ORGANISM: Corynebacterium glutamicum
<220> FEATURE:
<221> NAME/KEY: CDS
<222> LOCATION: (1)..(324)
<223> OTHER INFORMATION: brnE
<223> OTHER INFORMATION: ATCC14752

<400> SEQUENCE: 4 atg aca act gat ttc tcc tgt att ctc ctt gtt gtc gca gta tgt gca      48
Met Thr Thr Asp Phe Ser Cys Ile Leu Leu Val Val Ala Val Cys Ala
 1               5                  10                  15 gtc att act ttt gcg ctc cgg gcg gtt ccg ttc tta atc ctt aag ccc      96
Val Ile Thr Phe Ala Leu Arg Ala Val Pro Phe Leu Ile Leu Lys Pro
                20                  25                  30 cta cgt gaa tca caa ttt gtg ggc aaa atg gcg atg tgg atg cca gca    144
Leu Arg Glu Ser Gln Phe Val Gly Lys Met Ala Met Trp Met Pro Ala
        35                  40                  45 gga atc ctt gcc att ttg acc gca tca acg ttt cgc agc aat gcg ata    192
Gly Ile Leu Ala Ile Leu Thr Ala Ser Thr Phe Arg Ser Asn Ala Ile
    50                  55                  60 gat ctg aag act cta acc ttt ggt ctc att gcc gtt gcg att aca gtg    240
Asp Leu Lys Thr Leu Thr Phe Gly Leu Ile Ala Val Ala Ile Thr Val
65                  70                  75                  80
```

```
gtg gcg cat ctt ctt ggc ggt cga cgc acc ttg ttg agc gtt ggc gct    288
Val Ala His Leu Leu Gly Gly Arg Arg Thr Leu Leu Ser Val Gly Ala
             85                  90                  95 ggc acc atc gtt ttt gtt gga ctg gtg aat ctt ttc                     324
Gly Thr Ile Val Phe Val Gly Leu Val Asn Leu Phe
        100                 105

<210> SEQ ID NO 5
<211> LENGTH: 108
<212> TYPE: PRT
<213> ORGANISM: Corynebacterium glutamicum
<220> FEATURE:
<223> OTHER INFORMATION: ATCC14752

<400> SEQUENCE: 5

Met Thr Thr Asp Phe Ser Cys Ile Leu Leu Val Val Ala Val Cys Ala
  1               5                  10                  15

Val Ile Thr Phe Ala Leu Arg Ala Val Pro Phe Leu Ile Leu Lys Pro
             20                  25                  30

Leu Arg Glu Ser Gln Phe Val Gly Lys Met Ala Met Trp Met Pro Ala
         35                  40                  45

Gly Ile Leu Ala Ile Leu Thr Ala Ser Thr Phe Arg Ser Asn Ala Ile
     50                  55                  60

Asp Leu Lys Thr Leu Thr Phe Gly Leu Ile Ala Val Ala Ile Thr Val
 65                  70                  75                  80

Val Ala His Leu Leu Gly Gly Arg Arg Thr Leu Leu Ser Val Gly Ala
             85                  90                  95

Gly Thr Ile Val Phe Val Gly Leu Val Asn Leu Phe
        100                 105

<210> SEQ ID NO 6
<211> LENGTH: 1271
<212> TYPE: DNA
<213> ORGANISM: Corynebacterium glutamicum
<220> FEATURE:
<221> NAME/KEY: gene
<222> LOCATION: (101)..(853)
<223> OTHER INFORMATION: brnF
<221> NAME/KEY: gene
<222> LOCATION: (853)..(1176)
<223> OTHER INFORMATION: brnE
<223> OTHER INFORMATION: ATCC13032

<400> SEQUENCE: 6
gcgcgatcaa tggaatctag cttcatatat tgcacaatag cctagttgag gtgcgcaaac     60
tggcaacaaa actacccggc aattgtgtga tgattgtagt gtgcaaaaaa cgcaagagat    120
tcattcaagc ctggaggtgt cgccatccaa ggcagccctg gaaccagatg ataaaggtta    180
tcggcgctac gaaatcgcgc aaggtctaaa aacctccctt gctgcaggtt tgggcatgta    240
cccgattggt attgcgtttg gtctcttggt tattcaatac ggctacgaat ggtgggcagc    300
ccactgtttt ccggcctga ttttcgcggg ctccaccgaa atgctggtca tcgccctcgt    360
tgtgggcgca cgcccctgg cgccatcgc gctcaccaca ttgctggtga acttccgcca    420
cgtattctat gcgttttcat tcccgctgca tgtggtcaaa accccattg cccgtttcta    480 ttcggttttc gcgcttatcg acgaagccta cgcagtcact gcggccaggc ccgcaggctg    540
gtcggcgtgg cgacttatct caatgcaaat agcgtttcac tcctactggg tattcggcgg    600
tctcaccgga gtggcgatcg cagagttgat tccttttgaa attaagggcc tcgagttcgc    660
cctttgctct ctctttgtca cgctgacttt ggattcctgc cgaacgaaaa agcagatccc    720
```

-continued

```
ttctctgctg ctcgcaggtt tgagcttcac cattgctctt gtggtaattc caggtcaggc    780
cctatttgcg gcgctgctga tcttcttggg tctgttgacc atccggtact tcttcttggg    840
aaaggctgct aaatgacaac tgatttctcc tgtattctcc ttgttgtcgc agtatgtgca    900
gtcattactt ttgcgctccg ggcggttccg ttcttaatcc ttaagcccct acgtgaatca    960
caatttgtgg gcaaaatggc gatgtggatg ccagcaggaa tccttgccat tttgaccgca   1020
tcaacgtttc gcagcaatgc gatagatctg aagactctaa cctttggtct cattgccgtt   1080
gcgattacag tggtggcgca tcttcttggc ggtcgacgca ccttgttgag cgttggcgct   1140
ggcaccatcg ttttgttgg actggtgaat cttttctaaa actgcataaa taacaaaaat   1200
ccgcatgccc tcaatttgaa ggggatgcgg attttttaag gaacctagaa aaggcttaag   1260
cagacagcgc t                                                        1271
```

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 7
agcgctgtct gcttaagcct tttc                                            24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 8
gcgcgatcaa tggaatctag cttc                                            24

<210> SEQ ID NO 9
<211> LENGTH: 17
<212> TYPE: DNA
<213> ORGANISM: Artificial sequence
<220> FEATURE:
<223> OTHER INFORMATION: Description of artificial sequence: Universal
      Primer

<400> SEQUENCE: 9
gtaaaacgac ggccagt                                                    17

<210> SEQ ID NO 10
<211> LENGTH: 19
<212> TYPE: DNA
<213> ORGANISM: Artificial sequence
<220> FEATURE:
<223> OTHER INFORMATION: Description of artificial sequence: Reverse
      Primer

<400> SEQUENCE: 10
ggaaacagct atgaccatg                                                  19

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Primer

```
<400> SEQUENCE: 11
cgggtctaca ccgctagccc agg                                          23

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
cggtgcctta tccattcagg                                              20
```

NUCLEOTIDE SEQUENCES CODING FOR THE EXPORT OF BRANCHED CHAIN AMINO ACIDS, PROCESS FOR THE ISOLATION THEREOF AND USE THEREOF

CROSS REFERENCE TO RELATED APPLICATIONS

The present application claims priority under 35 U.S.C. §119 to German Application 199 51 708.8, filed on Oct. 27, 1999.

FIELD OF THE INVENTION

The present invention provides nucleotide sequences coding for the export of branched-chain amino acids, a process for the identification and isolation thereof and a process for the fermentative production of branched-chain amino acids using coryneform bacteria in which genes which code for the export of branched-chain amino acids are amplified.

BACKGROUND INFORMATION

The branched-chain amino acids L-isoleucine, L-valine and L-leucine are used in the pharmaceuticals industry, in human medicine and in animal nutrition.

It is known that branched-chain amino acids may be produced by fermentation of strains of coryneform bacteria, in particular *Corynebacterium glutamicum*. Due to their great significance, efforts are constantly being made to improve the production process. Improvements to the process may relate to measures concerning fermentation technology, for example stirring and oxygen supply, or to the composition of the nutrient media, such as for example sugar concentration during fermentation, or to working up of the product by, for example, ion exchange chromatography, or to the intrinsic performance characteristics of the microorganism itself.

The performance characteristics of these microorganisms are improved using methods of mutagenesis, selection and mutant selection. In this manner, strains are obtained which are resistant to antimetabolites, such as for example the isoleucine analogue isoleucine hydroxyamate (Kisumi M, Komatsubara S, Sugiura, M, Chibata I (1972) Journal of Bacteriology 110: 761–763), the valine analogue 2-thiazolealanine (Tsuchida T, Yoshinanga F, Kubota K, Momose H (1975) Agricultural and Biological Chemistry; Japan 39: 1319–1322) or the leucine analogue α-aminobutyrates (Ambe-Ono Y, Sato K, Totsuka K, Yoshihara Y, Nakamori S (1996) Bioscience Biotechnology Biochemistry 60: 1386–1387) or which are auxotrophic for regulatorily significant metabolites and produce branched-chain amino acids (Tsuchida T, Yoshinaga F, Kubota K, Momose H, Okumura S (1975) Agricultural and Biological Chemistry; Nakayama K, Kitada S, Kinoshita S (1961) Journal of General and Applied Microbiology, Japan 7: 52–69; Nakayama K, Kitada S, Sato Z, Kinoshita (191) Journal of General and Applied Microbiology, Japan 7: 41–51).

For some years, the methods of recombinant DNA technology have also been used for improvement of strains of Corynebacterium which produce branched-chain amino acids by amplifying individual biosynthesis genes for branched-chain amino acids and investigating the effect on branched-chain amino acid production. Review articles on this subject may be found inter alia in Kinoshita ("Glutamic Acid Bacteria", in: Biology of Industrial Microorganisms, Demain and Solomon (Eds.), Benjamin Cummings, London, UK, 1985, 115–142), Hilliger (BioTec 2, 40–44 (1991)), Eggeling (Amino Acids 6:261–272 (1994)), Jetten and Sinskey (Critical Reviews in Biotechnology 15, 73–103 (1995)), Sahm et al. (Annuals of the New York Academy of Science 782, 25–39 (1996)), and Eggeling et al., Journal of Biotechnology 56: 168–180 (1997)).

SUMMARY OF THE INVENTION

Object of the Invention

The inventors set themselves the object of providing novel measures for the improved fermentative production of branched-chain amino acids.

Description of the Invention

Branched-chain amino acids are used in the pharmaceuticals industry, in human medicine and in animal nutrition. There is accordingly general interest in providing novel improved processes for the production of branched-chain amino acids.

Any subsequent mention of branched-chain amino acids should be taken to mean in particular L-isoleucine, L-valine or L-leucine.

The present invention provides isolated polynucleotides containing at least one polynucleotide sequence selected from the group a) polynucleotide which is at least 70% identical to a polynucleotide which codes for a polypeptide containing at least one amino acid sequence SEQ ID no. 3 or 5, b) polynucleotide which codes for a polypeptide which contains an amino acid sequence which is at least 70% identical to the amino acid sequence of SEQ ID no. 3 or 5, c) polynucleotide which is complementary to the polynucleotides of a) or b) and d) polynucleotide containing at least 15 successive bases of the polynucleotide sequences of a), b) or c).

The present invention also provides preferably recombinant DNA replicable in coryneform bacteria and originating from Corynebacterium which contains at least the nucleotide sequences which code for the genes brnF and/or brnE, as shown in SEQ ID no. 1 and in SEQ ID no. 6.

The present invention also provides replicable DNA as described in a)–c) above containing:

(i) the nucleotide sequences shown in SEQ ID no. 1 or SEQ ID no. 6 which code for the genes brnE and/or brnF, or (ii) at least one sequence which matches the sequence (i) within the degeneration range of the genetic code, or (iii) at least one sequence which hybridises with the complementary sequence to sequences (i) or (ii) and optionally (iv) functionally neutral sense mutations in (i).

The present invention also provides polynucleotides as in a)–d) above which comprise recombinant DNA replicable in coryneform bacteria and contain containing at least one of the nucleotide sequences selected from those shown in SEQ ID no. 1, 2, 4 or 6 polypeptides as described in a)–d) above which comprimise recombinant DNA replicable in coryneform bacteria which code for polypeptides which contain at least one of the amino acid sequences as shown in SEQ ID no. 3 or 5 a vector containing the polynucleotide or polynucleotides as described in a)–c) above or the DNA sequence shown in SEQ ID no. 1 or SEQ ID no. 6.

and coryneform bacteria acting as host cell which contain the vector.

The present invention also provides polynucleotides which substantially consist of one polynucleotide sequence, which are obtainable by screening by means of hybridisation of a suitable gene library, which contains the complete genes having the polynucleotide sequences according to SEQ ID no. 1, 2, 4 or 6 with a probe which contains the sequence of the stated polynucleotides according to SEQ ID no. 1, 2, 4 or 6 or a fragment thereof and isolation of the stated DNA sequences.

Polynucleotide sequences according to the invention are suitable as hybridisation probes for RNA, cDNA and DNA in order to isolate full length cDNA which codes for isoleucine, leucine or valine export proteins and to isolate such cDNA or genes, the sequences of which exhibit a high level of similarity with that of the brnF and/or brnE gene.

Polynucleotide sequences according to the invention are furthermore suitable as primers, with the assistance of which, usingthe polymerase chain reaction (PCR), DNA of genes whichcode for isoleucine, leucine or valine export proteins may be produced.

Such oligonucleotides acting as probes or primers contain at least 30, preferably at least 20, very particularly preferably at least 15 successive nucleotides. Oligonucleotides having a length of at least 40 or 50 base pairs are also suitable.

"Isolated" means separated from its natural environment.

"Polynucleotide" generally relates to polyribonucleotides and polydeoxyribonucleotides, wherein the RNA or DNA may be unmodified or modified.

"Polypeptides" are taken to mean peptides or proteins which contain two or more aminoacids connected by peptide bonds.

The polypeptides according to the invention include the polypeptides according to SEQ ID no. 3 and/or 5, in particular those having the biological activity of transporting branched-chain amino acids and also those which are at least 70% identical to the polypeptides according to SEQ ID no. 3 and/or 5, preferably at least 80% and in particular 90% to 95% identical to the polypeptides according to SEQ ID no. 3 and/or 5 and exhibit the stated activity.

The present invention also provides coryneform microorganisms, in particular of the genus Corynebacterium, transformed by the introduction of the stated replicable DNA.

The invention furthermore relates to a process for the fermentative production of branched-chain amino acids using coryneform bacteria, which in particular already produce the branched-chain amino acids and in which the nucleotide sequences of the genes brnE and/or brnF which code for the export of branched-chain amino acids are amplified, in particular overexpressed.

In this connection, the term "amplification" describes the increase in the intracellular activity of one or more enzymes (proteins) in a microorganism, which enzymes are coded by the corresponding DNA, for example by increasing the copy number of the gene or genes, by using a strong promoter or a gene which codes for a corresponding enzyme (protein) having elevated activity and optionally by combining these measures.

The microorganisms, provided by the present inventions, may produce branched-chain amino acids from glucose, sucrose, lactose, mannose, fructose, maltose, molasses, starch, cellulose or from glycerol and ethanol. The microorganisms may comprise representatives of the coryneform bacteria in particular of the genus Corynebacterium. Within the genus Corynebacterium, *Corynebacterium glutamicum* may in particular be mentioned, which is known in specialist circles for its ability to produce L-amino acids.

Suitable strains of the genus Corynebacterium, in particular of the species *Corynebacterium glutamicum*, are in particular the known wild type strains

*Corynebacterium glutamicum* ATCC13032
*Brevibacterium flavum* ATCC14067
*Brevibacterium lactofermentum* ATCC13869 and
*Brevibacterium divaricatum* ATCC14020 and branched-chain amino acid producing mutants or strains produced therefrom, such as for example the isoleucine producing strains

*Corynebacterium glutamicum* ATCC14309
*Corynebacterium glutamicum* ATCC14310
*Corynebacterium glutamicum* ATCC14311
*Corynebacterium glutamicum* ATCC15168
*Corynebacterium ammoniagenes* ATCC 6871, such as for example the leucine producing strains

*Corynebacterium glutamicum* ATCC 21885
*Brevibacterium flavum* ATCC 21889 or such as for example the valine producing strains

*Corynebaccterium glutamicum* DSM 12455
*Corynebarcterium glutamicum* FERM-P 9325
*Brevibacterium lactofermentum* FERM-P 9324
*Brevibacterium lactofermentum* FERM-BP 1763.

The inventors succeeded in isolating the novel genes brnE and brnF from *Corynebacterium glutamicum*. The genes are isolated by initially producing a mutant of *C. glutamicum* which is defective with regard to brnF or brnE. To this end, a suitable starting strain, such as for example ATCC 14752 or ATCC 13032 is subjected to a mutagenesis process.

Classical mutagenesis processes are treatment with chemicals such as for example N-methyl-N-nitro-N-nitrosoguanidine or UV irradiation. Methods of this type for initiating mutation are generally known and may be found inter alia in Miller. (A Short Course in Bacterial Genetics, A Laboratory Manual and Handbook for *Escherichia coli* and Related Bacteria (Cold Spring Harbor Laboratory Press, 1992)) or in the manual "Manual of Methods for General Bacteriology" of the American Society for Bacteriology (Washington D.C., USA, 1981).

Another mutagenesis method is the transposon mutagenesis method which exploits the characteristic of a transposon to "jump" into DNA sequences, so disrupting or suppressing the function of the gene concerned. Transposons of coryneform bacteria are known in specialist circles. The erythromycin resistance tfansposon Tn5432 (Tauch et al., Plasmid (1995) 33: 168–179) and the chloramphenicol resistance transposon Tn5546 have accordingly been isolated from *Corynebacterium xerosis* strain M82B. Tauch et al. (Plasmid (1995) 34: 119–131 and Plasmid (1998) 40: 126–139) demonstrated that mutagenesis is possible with these transposons.

Another transposon is transposon Tn5531, which is described in Ankri et al. (Journal of Bacteriology (1996) 178: 4412–4419) and was used by way of example in the course of the present invention. Transposon Tn553l contains the aph3 kanamycin resistance gene and may be administered in form of the plasmid vector pCGL0040, which is shown in FIG. 1. The nucleotide sequence of transposon Tn5531 is freely available under the accession number U53587 from the National Center for Biotechnology Itformation (NCBI, Bethesda, Md., USA).

Once mutagenesis, preferably transposon mutagenesis, has been performed, a mutant defective with regard to brnF or brnE is sought. A mutant defective with regard to brnF or brnE is recognised by the fact that it exhibits good growth on minimal agar, but poor growth on minimal agar which has been supplemented with oligopeptides containing branched-chain amino acids, such as for example the dipeptide isoleucyl-isoleucine.

One example of such a mutant is strain ATCC14752brnE::Tn5531.

A strain produced in the stated manner may be used for cloning and sequencing the brnF and/or brnE gene.

To this end, a gene library of the bacterium under consideration may be constructed. The construction of gene libraries is described in generally known textbooks and manuals. Examples which may be mentioned are the textbook by Winnacker, Gene und Klone, Eine Einführung in die Gentechnologie (Verlag Chemie, Weinheim, Germany, 1990) or the manual by Sambrook et al., Molecular Cloning, A Laboratory Manual (Cold Spring Harbor Laboratory Press, 1989). One very well known gene library is that of *E. coli* K-12 strain W3110, which was constructed by Kohara et al. (Cell 50, 495–508 (1987)) in λ-vectors. Bathe et al. (Molecular and General Genetics, 252:255–265, 1996) describe a gene library of *C. glutamicum* ATCC13032, which was constructed using the cosmid vector SuperCos I (Wahl et al., 1987, Proceedings of the National Academy of Sciences USA, 84:2160.2164) in *E. coli* K-12 strain NM554 (Raleigh et al., 1988, Nucleic Acids Research 16:1563–1575). Vectors suitable for the present invention are those which replicate in coryneform bacteria, preferably *Corynebacterium glutamicum*. Such vectors are known from the prior art; one example which may be mentioned is the plasmid vector pZ1, which is described in Menkel et al. (Applied and Environmental Microbiology (1989) 64: 549–554). The gene library obtained in the stated manner is then transferred by transformation or electroporation into the indicator strain which is defective with regard to brnF or brnE and those transformants are sought which are capable of growing on minimal agar in the presence of oligopeptides containing branched-chain amino acids. The cloned DNA fragment may then be subjected to sequence analysis.

When a mutant produced by Tn5531 mutagenesis of a coryneform bacterium, such as for example strain ATCC 14752brnE::Tn5531, is used, the brnE::Tn5531 allele may be directly cloned and isolated by exploiting the kanamycin resistance gene aph3 contained therein. Known cloning vectors, such as for example pUC18 (Norrander et al., Gene (1983) 26: 101–106 and Yanisch-Perron et al., Gene (1985) 33: 103–119) are used for this purpose. Suitable cloning hosts are in particular those strains of *E. coli* with restriction and recombination defects. One example of such a strain is the strain DH5αmcr, which has been described by Grant et al. (Proceedings of the National Academy of Sciences USA, 87 (1990) 4645–4649). Transformant selection proceeds in the presence of kanamycin. The plasmid DNA of the resultant transformants is then sequenced. The dideoxy chain termination method of Sanger et al. (Proceedings of the National Academy of Sciences of the United States of America USA (1977) 74: 5463–5467) may be used for this purpose. Using this method, the genes located upstream and downstream from the Tn5531 insertion site are obtained. The nucleotide sequences obtained are then analysed and assembled using commercially available sequence analysis software, such as for example the Lasergene package (Biocomputing Software for Windows, DNASTAR, Madison, USA) or the HUSAR package (release 4.0, EMBL, Heidelberg, Germany).

This is the method which was used to obtain the novel DNA sequences of *C. glutamicum* which code for the export of branched-chain amino acids and are provided by the present invention as SEQ ID no. 1. SEQ ID no. 2 and SEQ ID no. 4 show the coding regions of the genes brnF and brnE. SEQ ID no. 3 and SEQ ID no. 5 show the amino acid sequences of the gene products obtained respectively from SEQ ID no. 1 or from SEQ ID no. 2 and SEQ ID no. 4.

Coding DNA sequences arising from the degeneracy of the genetic code are also provided by the present invention. DNA sequences which hybridise with SEQ ID no. 1 or parts of SEQ ID no. 1 are similarly provided by the invention. Conservative substitutions of amino,acids in proteins, for example the substitution of glycine for alanine or of aspartic acid for glutamic acid, are known in specialist circles as "sense mutations", which result in no fundamental change in activity of the protein, i.e. they are functionally neutral. It is furthermore known that changes to the N and/or C terminus of a protein do not substantially impair or may even stabilise the function thereof. The person skilled in the art will find information in this connection inter alia in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences arising in a corresponding manner from SEQ ID no. 2 or SEQ ID no. 4 are also provided by the present invention.

Using the nucleotide sequence shown in SEQ ID no. 1, it is possible to synthesise suitable primers and these may then be used with the assistance of the polymerase chain reaction (PCR) to amplify the brnF and brnE genes of various coryneform bacteria and strains. The person skilled in the art will find instructions in connection inter alia in the textbook by Gait, Oligonucleotide synthesis: a practical approach (IRL Press, Oxford, UK, 1984) and in Newton and Graham, PCR (Spektrum Akademischer Verlag, Heidelberg, Germany, 1994). Alternatively, the nucleotide sequence shown in SEQ ID no. 1 or parts thereof may be used as a probe to search for brnF and/or brnE genes in gene libraries, in particular of coryneform bacteria. The person skilled in the art will find instructions in this connection inter alia in the manual "The DIG System Users Guide for Filter Hybridization" from Boehringer Mannheim GmbH (Mannheim, Germany, 1991) and in Liebl et al. (International Journal of Systematic Bacteriology (1991) 41: 255–260). DNA fragments containing brnE and brnF genes amplified in this manner are then cloned and sequenced.

The DNA sequence of the genes brnF and brnE of strain ATCC 13032 shown in SEQ ID no. 6 was obtained in this manner and is also provided by the present invention.

The inventors discovered that coryneform bacteria produce branched-chain amino acids in an improved manner once the brnF and/or brnE export gene has been overexpressed.

Overexpression may be achieved by increasing the copy number of the corresponding genes or by mutating the promoter and regulation region or the ribosome-binding site located upstream from the structural gene. Expression cassettes incorporated upstream from the structural gene act in the same manner. It is additionally possible to increase expression during the fermentative production of branched-chain amino acids by inducible promoters. Expression is also improved by measures to extend the lifetime of the mRNA. Enzyme activity is moreover amplified by preventing degradation of the enzyme protein. The genes or gene constructs may either be present in plasmids in a variable copy number or be integrated in the chromosome and amplified. Alternatively, overexpression of the genes concerned may also be achieved by modifying the composition of the nutrient media and culture conditions.

The person skilled in the art will find guidance in this connection inter alia in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European patent EP-B 0 472 869, in U.S. Pat. No. 4,601,893, in Schwarzer and Pühler (Bio/Technology 9, 84–87 (1991)), in Reinscheid et al. (Applied and Environmental Microbiology 60, 126–132 (1994)), in LaBarre et al. (Journal of Bacteriology 175, 1001–1007 (1993)), in patent application WO 96/15246, in Malumbres et al. (Gene 134, 15–24 (1993)), in Japanese published patent application JP-A-10-229891, in Jensen and Hammer (Biotechnology and Bioengineering 58, 191–195 (1998)), in Makrides (Microbiological Reviews 60:512–538 (1996)) and in known textbooks of genetics and molecular biology.

By way of example, the genes brnF and brnE according to the invention were overexpressed with the assistance of plasmids. Suitable plasmids are those which are replicated in coryneform bacteria. Numerous known plasmid vectors, such as for example pZ1 (Menkel et al., Applied and Environmental Microbiology (1989) 64: 549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors, such as for example those based on pCG4. (U.S. Pat. No. 4,489,160), or pNG2 (Serwold-Davis et. al., FEMS Microbiology Letters 66, 119–124 (1990)), or pAG1 (U.S. Pat. No. 5,158,891) may be used in the same manner.

It may additionally be advantageous for the production of branched-chain amino acids, in addition to novel brnF and brnE genes, to overexpress one or more genes which code for further enzymes of the known biosynthetic pathway of branched-chain amino acidsor enzymes of anaplerotic metabolism, or enzymes of the citric acid cycle.

Thus, for example, for theproduction of L-isoleucine the hom gene (Peoples et al., Molecular Microbiology 2, 63–72 (1988)) which codes for homoserine dehydrogenase or the hom$^{dr}$ allele (Archer et al., Gene 107, 53–59 (1991)) which codes for a "feed back resistant" homoserine dehydrogenase may simultaneously be overexpressed or the ilvA gene (Möckel et al., Journal of Bacteriology (1992) 8065–8072)) which codes for threonine dehydratase or the ilvA(Fbr) allele (Möckel et al., (1994) Molecular Microbiology 13: 833–842) which codes for a "feed back resistant" threonine dehydratase may simultaneously be overexpressed or the genes ilvBN (Keilhauer et al., (1993) Journal of Bacteriology 175: 5595–5603) which code for acetohydroxy acid synthase may simultaneously be overexpressed or the ilvD gene (Sahm und Eggeling (1999) Applied and Environmental Microbiology 65: 1973–1979) which codes for dihydroxy acid dehydratase may simultaneously be overexpressed or the pyc gene (DE-A-19 831 609) which codes for pyruvate carboxylase may simultaneously be overexpressed or the mqo gene (Molenaar et al., European Journal of Biochemistry 254, 395–403 (1998)) which codes for malate:quinone oxidoreductase may simultaneously be overexpressed.

Thus, for example, for the production of L-leucine, the leuA gene (Pátek et al., Applied Environmental Microbiology 60 (1994) 133–140) which codes for isopropyl malate synthase or an allele which codes for a "feed back resistant" isopropyl malate synthase may simultaneously be overexpressed or the leuC and leuD genes (Pátek et al., Applied Environmental Microbiology 60 (1994) 133–140) which code for isopropyl malate dehydratase may simultaneously be overexpressed or the leuB gene (Pátek et al., Applied Environmental Microbiology 60 (1994) 133–140) which codes for isopropyl malate dehydrogenase may simultaneously be overexpressed or the genes ilvBN (Keilhauer et al., (1993) Journal of Bacteriology 175: 5595–5603) which code for acetohydroxy acid synthase may simultaneously be overexpressed or the ilvD gene (Sahm und Eggeling (1999) Applied and Environmental Microbiology 65: 1973–1979) which codes for dihydroxy acid dehydratase may simultaneously be overexpressed or the mqo gene (Molenaar et al., European Journal of Biochemistry 254, 395–403 (1998)) which codes for malate:quinone oxidoreductase may simultaneously be overexpressed.

Thus, for example, for the production of L-valine the genes ilvBN (Keilhauer et al., (1993) Journal of Bacteriology 175: 5595–5603) which code for acetohydroxy acid synthase may simultaneously be overexpressed or the ilvD gene (Sahm und Eggeling (1999) Applied and Environmental Microbiology 65: 1973–1979) which codes for dihydroxy acid dehydratase may simultaneously be overexpressed or the mqo gene (Molenaar et al., European Journal of Biochemistry 254, 395–403 (1998)) which codes for malate:quinone oxidoreductase may simultaneously be overexpressed.

It may furthermore be advantageous for the production of branched-chain amino acids, in addition to overexpressing the brnE and/or brnF gene, to suppress unwanted secondary reactions (Nakayama: "Breeding of Amino Acid. Producing Microorganisms", in: Overproduction of Microbial Products, Krumphanzl, Sikyta, Vahek (eds.), Academic Press, London, UK, 1982).

For the purposes of branched-chain amino acid production, the microorganisms according to the invention may be cultured continuously or discontinuously using the batch process or the fed batch process or repeated fed batch process. A summary of known culture methods is given in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must adequately satisfy the requirements of the particular strains. Culture media for various microorganisms are described in "Manual of Methods for General Bacteriology" from American Society for Bacteriology (Washington D.C., USA, 1981). Carbon sources which may be used include sugars and carbohydrates, such as for example glucose, sucrose, lactose, fructose, maltose, molasses, starch and cellulose, oils and fats, such as for example soya oil, sunflower oil, peanut oil and coconut oil, fatty acids, such as for example palmitic acid, stearic acid and linoleic acid, alcohols, such as for example glycerol and ethanol, and organic acids, such as for example acetic acid. These substances may be used individually or as a mixture. Nitrogen sources which may be used comprise organic compounds containing nitrogen, such as peptones, yeast extract, meat extract, malt extract, corn steep liquor, soya flour and urea or inorganic compounds, such as ammonium sulfate, ammonium chloride, ammonium phosphate, ammonium carbonate and ammonium nitrate. The nitrogen sources may be used individually or as a mixture. Phosphorus sources which may be used are phosphoric acid, potassium dihydrogen phosphate or dipotassium hydrogen phosphate or the corresponding salts containing sodium. The culture medium must furthermore contain metal salts, such as for example magnesium sulfate or iron sulfate, which are necessary for growth. Finally, essential growth-promoting substances such as amino acids and vitamins may also be used in addition to the above-stated substances. Suitable precursors may furthermore be added to the culture medium. The stated feed substances may be added to the culture as a single batch or be fed appropriately during cultivation.

Basic compounds, such as sodium hydroxide, potassium hydroxide, ammonia or ammonia water, or acidic compounds, such as phosphoric acid or sulfuric acid, are used appropriately to control the pH of the culture. Antifoaming agents, such as for example fatty acid polyglycol esters, may be used to control foaming. Suitable selectively acting substances, such as for example antibiotics, may be added to the medium in order to maintain plasmid stability. Oxygen or gas mixtures containing oxygen, such as for example air, are introduced into the culture in order to maintain aerobic conditions. The temperature of the culture is normally from 20° C. to 45° C. and preferably from 25° C. to 40° C. The culture is continued until the maximum quantity of branched-chain amino acids has formed. This objective is normally achieved within 10 hours to 160 hours.

The branched-chain amino acids may be analysed by anion exchange chromatography with subsequent ninhydrin derivatisation, as described in Spackman et al. (Analytical Chemistry, 30, (1958), 1190) or by reversed phase HPLC, as described in Lindroth et al. (Analytical Chemistry (1979) 51: 1167–1174).

The following microorganism has been deposited with Deutschen Sammlung für Mikrorganismen und Zellkulturen (DSMZ, Braunschweig, Germany) in accordance with the Budapest Treaty:

Escherichia coli strain GM2929pCGL0040 as DSM 12839

DETAILED DESCRIPTION OF THE INVENTION

The present invention is illustrated in greater detail by the following practical examples.

Isolation of plasmid DNA from *Escherichia coli* and all restriction, Klenow and alkaline phosphatase treatment techniques were performed in accordance with Sambrook et al. (Molecular cloning. A laboratory manual (1989) Cold Spring Harbour Laboratory Press). Unless otherwise stated, the transformation of *Escherichia coli* was performed in accordance with Chung et al. (Proceedings of the National Academy of Sciences of the United States of America (1989) 86: 2172–2175).

EXAMPLE 1

Cloning and Sequencing of the brnF and brnE Gene of *Corynebacterium Glutamicum* ATCC 14752
1. Transposon Mutagenesis The strain *Corynebacterium glutamicum* ATCC 14752 was subjected to mutagenesis with transposon Tn5531, the sequence of which is deposited under accession number U53587 in the nucleotide database of the National Center for Biotechnology Information (Bethesda, USA). The plasmid pCGL0040, which contains the assembled transposon Tn5531 (Ankri et al., Journal of Bacteriology (1996) 178: 4412–4419), was isolated from the methylase-defective *E. coli* strain GM2929pCGL0040. (*E. coli* GM2929: Palmer et al., Gene. (1994) 143: 1–12). The strain *Corynebacterium glutamicum* ATCC 14752 was transformed with plasmid pCGL0040 by means of electroporation (Haynes et al., FEMS Microbiology Letters ,(1989) 61: 329–334). Clones in which transposon Tn5531 had been integrated into the genome were identified by their kanamycin resistance on LBHIS agar plates containing 15 μg/mL of kanamycin (Liebl et al., FEMS Microbiology Letters (1989) 65: 299–304). In this manner, 2000 clones were obtained, which were tested for delayed growth in the presence of isoleucyl-isoleucine. To this end, all the clones were individually transferred onto CXKII minimal medium agar plates with and without 3 mM isoleucyl-isoleucine. The medium was identical to the CGXII medium described in Keilhauer et al. (Journal of Bacteriology (1993) 175: 5593–5603), but additionally contained 25 μg/mL of kanamycin and 15 g/L of agar. The composition of the medium described by Keilhauer et al. is shown in Table 1.

TABLE 1

Composition of medium CGXII

| Component | Concentration |
| --- | --- |
| $(NH_4)_2SO_4$ | 20 g/L |
| Urea | 5 g/L |
| $KH_2PO_4$ | 1 g/L |
| $K_2HPO_4$ | 1 g/L |
| $MgSO_4 \times 7\ H_2O$ | 0.25 g/L |
| 3-morpholinopropanesulfonic | 42 g/L |
| $CaCl_2$ | 10 mg/L |
| $FeSO_4 \times 7\ H_2O$ | 10 mg/L |
| $MnSO_4 \times H_2O$ | 10 mg/L |
| $ZnSO_4 \times 7H_2O$ | 1 mg/L |
| $CuSO_4$ | 0.2 mg/L |
| $NiCl_2 \times 6\ H_2O$ | 0.02 mg/L |
| Biotin | 0.2 mg/L |
| Glucose | 40 g/L |
| Protocatechuic acid | 30 mg/L |

The agar plates were incubated at 30° C. and growth inspected after 12, 18 and 24 hours. A transposon mutant was obtained which, in the absence of isoleucyl-isoleucine, grew in a manner comparable with that of the initial strain *Corynebacterium glutamicum* ATCC 14752, but exhibited delayed growth in the presence of 3 mM isoleucyl-isoleucine. This was designated ATCC14752brnF::Tn5531.
2. Cloning and Sequencing of the Insertion Site of Tn 5531 in ATCC14752brnF::Tn5531

In order to clone the insertion site located downstream from transposon Tn5531 of the mutant described in Example 1.1, the chromosomal DNA of this mutant strain was first isolated as described in Schwarzer et al. (Bio/Technology (1990) 9: 84–87) and 400 ng thereof were cut with the restriction endonuclease EcoRI. The complete restriction batch was ligated into the vector pUC 18 (Norander et al., Gene (1983) 26: 101–106), likewise linearised with EcoRI, from Roche Diagnostics (Mannheim, Germany). The *E. coli* strain DH5amcr (Grant et al., Proceedings of the National Academy of Sciences of the United States of America (1990) 87: 4645–4649) was transformed with the entire ligation batch by means of electroporation (Dower et al., Nucleic Acid Research (1988) 16: 6127–6145). Transformants in which the insertion sites of transposon Tn5531 were present in cloned form on the vector pUC 18 were identified by means of the carbenicillin and kanamycin resistance on LB agar plates containing 50 μg/mL of carbenicillin and 25 μg/mL of kanamycin. The plasmids were prepared from three of the transformants and the size of the cloned inserts determined by restriction analysis. The nucleotide sequence of the insertion site on one of the plasmids having an insert of a size of approx. 7.2 kb was determined using the dideoxy chain termination method of Sanger et al. (Proceedings of the National Academy of Sciences of the United States of America (1977) 74: 5463–5467). To this end, 1.3 kb of the insert were sequenced starting from the following oligonucleotide primer:

5'-CGG GTC TAC ACC GCT AGC CCA GG-3' (SEQ ID NO: 11). 990131 BT 25,

In order to identify the insertion site located upstream from the transposon, the chromosomal DNA of the mutants was cut with the restriction endonuclease PstI and ligated into vector pUC 18 which had been linearised with PstI. The remainder of the cloning operation was performed as described above. The nucleotide sequence of the insertion site on one of the plasmids having an insert of a size of approx. 4.8 kb was determined using the dideoxy chain termination method of Sanger et al. (Proceedings of the National Academy of Sciences of the United States of America (1977) 74: 5463–5467). To this end, 1.6 kb of the insert were sequenced starting from the following oligonucleotide primer: 5'-CGG TGC CTT ATC CAT TCA GG-3' (SEQ ID NO: 12).

The nucleotide sequences obtained were analysed and assembled using the Lasergene package (Biocomputing Software for Windows, DNASTAR, Madison, USA). This nucleotide sequence is reproduced as SEQ ID no. 1. Analysis identified two open reading frames of a length of 753 bp and 324 bp, which are shown as SEQ ID no. 2 and SEQ ID no. 4. The corresponding genes were designated brnF and brnE. The associated gene products comprise 251 and 108 amino acids and are reproduced as SEQ ID no. 3 and SEQ ID no. 5.

EXAMPLE 2

Cloning and Sequencing of the brnF and brnE Genes From *Corynebacterium Glutamicum* ATCC 13032

The genes brnE and brnF from strain ATCC 13032 were cloned into the *E. coli* cloning vector pUC 18 (Norrander et al., Gene (1983) 26: 101–106, Roche Diagnostics, Mannheim, Germany). Cloning was performed in two steps. The genes from *Corynebacterium glutamicum* ATCC 13032 were initially amplified by a polymerase chain reaction (PCR) by means of the following oligonucleotide primer derived from SEQ ID no. 1.

brnE, brnF, -forward:
5'-(AGC GCT GTC TGC TTA AGC CTT TTC)-3' (SEQ ID NO: 7)
brnE, brnF, -reverse:
5'-(GCG CGA TCA ATG GAA TCT AGC TTC)-3' (SEQ ID NO: 8)

The PCR reaction was performed in 30 cycles in the presence of 200 μM of deoxynucleotide triphosphates (dATP, dCTP, dGTP, dTTP), a 1 μM portion of the corresponding oligonucleotide, 100 ng of chromosomal DNA from *Corynebacterium glutamicum* ATCC 13032, 1/10 volume of 10×reaction buffer and 2.6 units of a heat-stabilised Taq/Pwo DNA polymerase mixture (Expand High Fidelity PCR System from Roche Diagnostics, Mannheim, Germany) in a thermocycler (PTC-100, MJ Research Inc., Watertown, USA) under the following conditions: 94° C. for 30 seconds, 58° C. for 30 seconds and 72° C. for 2 minutes.

The amplified fragment of a size of approx. 1.3 kb was then ligated into the SmaI restriction site of the vector pUC 18 using the SureClone Ligation Kit (Amersham Pharmacia Biotech, Uppsala, Sweden) in accordance with the manufacturer's instructions. The *E. coli* strain DH5amcr (Grant et al., Proceedings of the National Academy of Sciences of the United States of America (1990) 87: 4645–4649) was transformed with the entire ligation batch. Transformants were identified by means of the carbenicillin resistance thereof on LB agar plates containing 50 μg/mL of carbenicillin. The plasmids were prepared from 8 of the transformants and the presence of the 1.3 kb PCR fragment as an insert was determined by restriction analysis. The resultant recombinant plasmid is hereinafter designated pUC18brnEF.

The nucleotide sequence of the 1.3 kb PCR fragment in plasmid pUC18brnEF was determined using the dideoxy chain termination method of Sanger et al. (Proceedings of the National Academy of Sciences of the United States of America (18) 1977: 74–5463). To this end, the complete insert of pUC18brnEF was sequenced using the following primer from Roche Diagnostics (Mannheim; Germany).

Universal primer:
5'-GTA AAA CGA CGG CCA GT-3' (SEQ ID NO: 9)
Reverse primer:
5'-GGA AAC AGC TAT GAC CAT G-3' (SEQ ID NO: 10)

The resultant nucleotide sequence is reproduced as SEQ ID no. 6. The nucleotide sequence obtained was analysed using the Lasergene package (Biocomputing Software for Windows, DNASTAR, Madison, USA).

Figure 1:
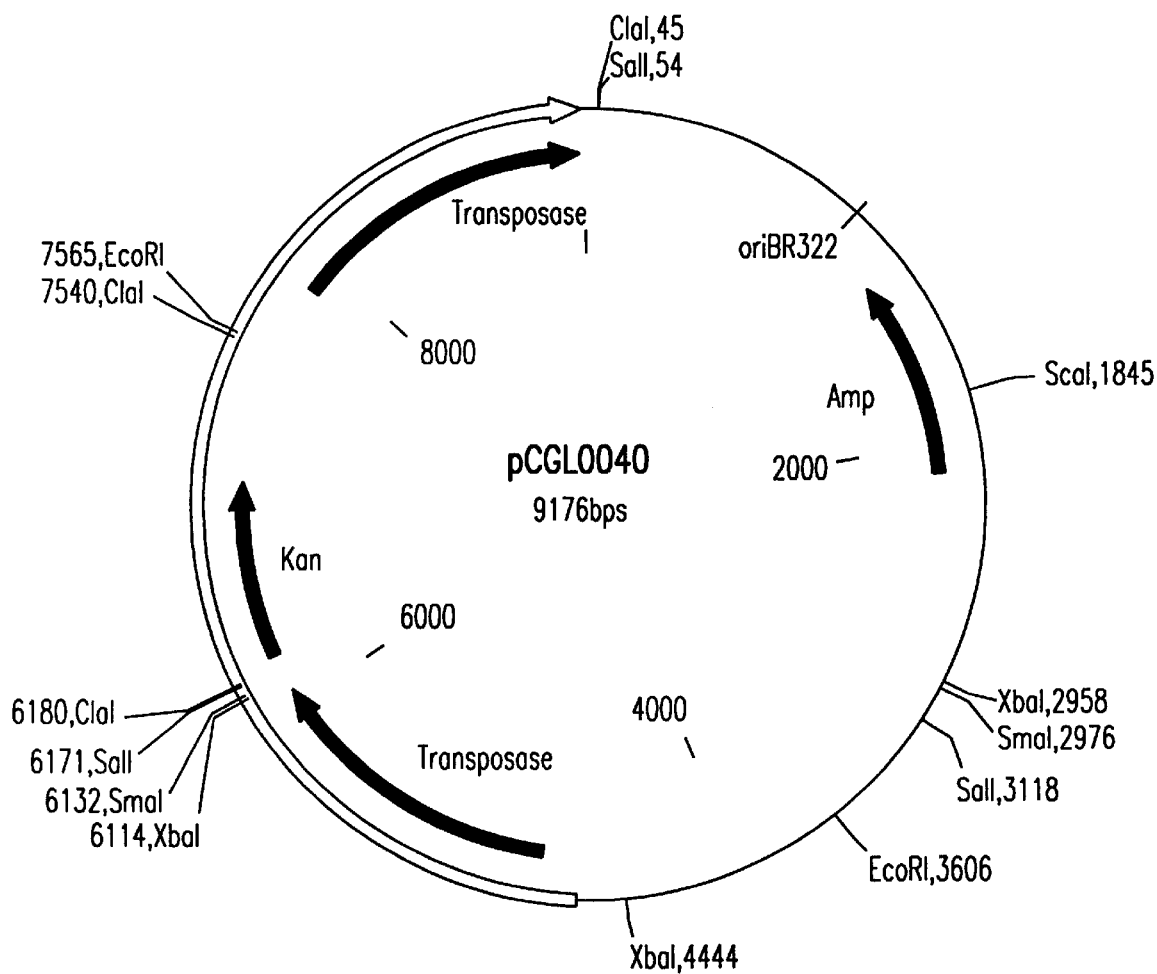
FIG. 1: Map of plasmid PCGL0040 containing transposon Tn5531. The transposon is indicated as the unshaded arrow.

The lengths stated should be considered to be approximate. The abbreviations and terms used have the following meaning:

EcoRI: Restriction endonuclease from *Escherichia coli*
XbaI: Restriction endonuclease from *Xanthomonas badrii*
ClaI: Restriction endonuclease from *Caryophanum latum*
SalI: Restriction endonuclease from *Streptomyces albus*
ScaI: Restriction endonuclease from *Streptomyces caespitosus*
SmaI: Restriction endonuclease from *Serratia marcescens*
Amp: Ampicillin resistance gene
Kan: Kanamycin resistance gene
oriBR322: Replication region of plasmid pBR322

What is claimed is:

1. An isolated polynucleotide consisting of a nucleotide sequence encoding a polypeptide consisting essentially of the amino acid sequence of SEQ ID NO:3 or SEQ ID NO:5.

2. An isolated polynucleotide consisting essentially of a nucleotide sequence selected from the group consisting of: SEQ ID NO:1; SEQ ID NO:1, from nucleotides 101 to 1176; SEQ ID NO:2; and SEQ ID NO:4.

3. The isolated polynucleotide of claim 2, wherein said polynucleotide consists of a nucleotide sequence selected from the group consisting of: SEQ ID NO:1; SEQ ID NO:1, from nucleotides 101 to 1176; SEQ ID NO:2; and SEQ ID NO:4.

4. A vector comprising the polynucleotide of any one of claims 1, 2 or 3.

5. A host cell transformed with the vector of claim 4.

6. A vector for the expression of brnE, brnF or both, said vector comprising:
   (a) a promoter; and
   (b) the polynucleotide of any one of claims 1, 2 or 3 joined to said promoter.

7. A bacterial host cell transformed with the vector of claim 6.

8. The bacterial host cell of claim 7, wherein said bacterial host is a strain of *Corynebacterium glutamicum*.

9. An isolated polynucleotide consisting of a nucelotide sequence encoding a protein consisting essentially of the amino acid sequence encoded by either nucleotides 101–853 or 853–1176 of SEQ ID NO:6.

10. An isolated polynucleotide consisting essentially of a nucleotide sequence selected from the group consisting of: SEQ ID NO:6; nucleotides 101–853 of SEQ ID NO:6; and nucleotides 853–1176 SEQ ID NO:6.

11. The isolated polynucleotide of claim 10, wherein said polynucleotide consists of a nucleotide sequence selected from the group consisting of: SEQ ID NO:6; nucleotides 101–853 of SEQ ID NO:6; and nucleotides 853–1176 SEQ ID NO:6.

12. A vector comprising the polynucleotide of any one of claims 9, 10 or 11.

13. A host cell transformed with the vector of claim 12.

14. A vector for the expression of brnE, brnF or both, said vector comprising:
   (a) a promoter; and
   (b) the polynucleotide of any one of claims 9, 10 or 11 joined to said promoter.

15. A bacterial host cell transformed with the vector of claim 14.

16. The bacterial host cell of claim 15, wherein said bacterial host is a strain of *Corynebacterium glutamicum*.

17. An isolated polynucleotide comprising:
   (a) a sequence consisting of nucleotides encoding a first polypeptide consisting essentially of the amino acid sequence of SEQ ID NO:3; and
   (b) a sequence consisting of nucleotides encoding a second distinct polypeptide consisting essentially of the amino acid sequence of SEQ ID NO:5.

18. An isolated polynucleotide consisting essentially of the nucleotide sequence of SEQ ID NO:2 and SEQ ID NO:4.

19. The isolated polynucleotide of claim 17, wherein said polynucleotide is a vector for expressing both brnF and brnE and further comprises at least one promoter.

20. A vector for the expression of both brnF and brnE, said vector comprising:
   (a) a promoter; and
   (b) the polynucleotide of claim 18.

21. A bacterial host cell transformed with the vector of either claim 19 or claim 20.

22. The bacterial host cell of claim 21, wherein said bacterial host is a strain of *Corynebacterium glutamicum*.

* * * * *